(12) United States Patent
Wu et al.

(10) Patent No.: US 7,262,051 B2
(45) Date of Patent: Aug. 28, 2007

(54) USE OF BISCISTRONIC DNA CONSTRUCTS FOR IDENTIFYING COMPOUNDS THAT INHIBIT IRES-DEPENDENT TRANSLATION

(75) Inventors: Tzong-Yuan Wu, Panchiao (TW); Tsu-An Hsu, Taipei (TW); Shin-Ru Shih, Taoyuan (TW); Suey-Sheng Kao, Taipei (TW); Tzyy-Rong Jinn, Nantou (TW); Shin-Jhan Zeng, Kaohsiung (TW); Ying-Ju Chen, Shinyuan Township, Pingtung County (TW)

(73) Assignee: Chung Yuan Christian University (TW)

( * ) Notice: Subject to any disclaimer, the term of this patent is extended or adjusted under 35 U.S.C. 154(b) by 287 days.

(21) Appl. No.: 10/913,269

(22) Filed: Aug. 6, 2004

(65) Prior Publication Data
US 2006/0024680 A1 Feb. 2, 2006

(30) Foreign Application Priority Data
Jul. 27, 2004 (TW) .............................. 93122453 A

(51) Int. Cl.
*C12N 15/63* (2006.01)
*C12Q 1/68* (2006.01)
*C12P 21/00* (2006.01)

(52) U.S. Cl. .................. 435/320.1; 435/5; 435/71.1
(58) Field of Classification Search .............. 435/320.1
See application file for complete search history.

(56) References Cited

U.S. PATENT DOCUMENTS

| 5,738,985 | A * | 4/1998 | Miles et al. ............... 435/5 |
| 6,623,961 | B2 * | 9/2003 | Miles et al. ............... 435/370 |
| 6,667,152 | B2 * | 12/2003 | Miles et al. ............... 435/5 |
| 6,777,179 | B2 * | 8/2004 | Miles et al. ............... 435/5 |
| 7,045,284 | B2 * | 5/2006 | Miles et al. ............... 435/5 |
| 2002/0160976 | A1 * | 10/2002 | Miles et al. ............... 514/44 |

OTHER PUBLICATIONS

Jubin et al. J. Infec. Diseas. 2000, vol. 181, pp. 331-334.*

* cited by examiner

*Primary Examiner*—Bruce R. Campell
*Assistant Examiner*—Bao Qun Li
(74) *Attorney, Agent, or Firm*—The Webb Law Firm

(57) ABSTRACT

The present invention relates to use of bicistronic DNA constructs for identifying compounds that inhibits IRES-dependent translation activity of an infectious enterovirus (EV) or encephalomyocarditis virus (EMCV) without affecting CAP-dependent translation activity of a host subject. The compounds thus identified are useful in preparation of a medicament for treating EV or EMCV infection.

4 Claims, 5 Drawing Sheets

A

B

C

USE OF BISCISTRONIC DNA CONSTRUCTS FOR IDENTIFYING COMPOUNDS THAT INHIBIT IRES-DEPENDENT TRANSLATION

BACKGROUND

1. Field of Invention

The present invention relates to use of bicistronic DNA constructs for identifying compounds that inhibits IRES-dependent translation activity of an infectious enterovirus (EV) or encephalomyocarditis virus (EMCV) without affecting CAP-dependent translation activity of a host subject. The compounds thus identified are useful in preparation of a medicament for treating an EV or EMCV infection.

2. Description of Related Art

Picornaviruses such as polioviruses, enterovirus, and encephalomyocarditis virus, are single stranded, plus-sense RNA viruses, which multiply in the cytoplasm of infected host cells by a unique mechanism involving internal entry of ribosomes near the initiator AUG (Pelletier et al., (1988) Nature 334, 320-325). Recent studies demonstrated that internal entry of ribosomes requires an element located between nucleotides 320-631 within the 5'UTR of poliovirus RNA (Pelletier et al., supra). This sequence element has been termed a ribosome landing pad (RLP) or, more generally, internal ribosome entry site (IRES). The picorna-related virus, such as hepatitis A and C, have also been shown to utilize internal ribosome entry site for translation initiation (Kohara et al., (1992) J Virol 66, 1476-1483 and Glass et al., (1993) Virology 193, 842-852) Furthermore, reports indicated that IRES sequence of Theiler's murine encephalomyelitis virus (TEMV) plays an important role on the virulence of the infectious virus (Sarnow (2003) Journal of Virology, 77, 2801-2806). For example, GDVII strains of TEMV with mutation on their IRES sequences are less virulent that those possess natural IRES sequences (Pilipenko, (2001) EMBO J. 20, 6899-6908). Taking together, the results above suggested that inhibition of IRES-dependent translation might be useful in treating these viral infections.

Inventors of this application unexpectedly found that bicistronic DNA constructs of infectious virus such as EV and EMCV may be used as a screening tool to identify compounds that inhibit IRES-dependent translation activities of these infectious viruses. The compounds thus identified, e.g., amantadine, will be useful in preparation of a medicament for treating EV or EMCV infection.

SUMMARY

This invention relates to use of bicistronic DNA constructs for identifying compounds that inhibits IRES-dependent translation activity of an infectious EV or EMCV while leaving CAP-dependent translation activity of a host subject unaffected. The compounds thus identified are useful in preparation of a medicament for treating EV or EMCV infection.

In one aspect, the invention features a method of identifying a candidate compound that inhibits IRES-dependent translation activity of an infectious EV or EMCV while leaving CAP-dependent translation activity of a host subject unaffected using bicistronic DNA constructs containing IRES of EV or EMCV. The method includes (1) contacting a candidate compound with a system (a cell system or a cell-free system) containing a bicistronic DNA construct containing IRES of EV or EMCV, wherein said bicistronic DNA construct comprises in sequence, a first reporter gene, which is CAP-dependent initiated, and a second reporter gene, which is IRES-dependent initiated; and (2) determining a level of said first reporter gene and said second reporter gene expression or protein activity in the system, if the level of the first reporter gene expression or protein activity is relatively unaffected while at the same time the level of the second reporter gene is significantly reduced, indicates that the candidate compound inhibits the IRES translation activity without affecting the CAP-dependent translation. Such a compound can be any molecule, e.g., an anti-sense RNA, an antibody or its variant, or a non-peptidyl molecule. A compound thus identified is amantadine.

In another aspect, this invention features a pharmaceutical composition comprising a pharmaceutically acceptable carrier and a therapeutically effective amount of a compound identified by the method of this invention. The compound, when administering to a subject in need thereof, inhibits the IRES translation activity of an infectious virus without affecting the CAP-dependent translation activity of a host subject. The pharmaceutical composition is useful in treating EV or EMCV infection.

Also within the scope of the invention is a method for treating EV or EMCV infection. The method comprises administering to a subject in need thereof, a pharmaceutical composition comprising a pharmaceutically acceptable carrier and a therapeutically effective amount of a compound identified by the method of this invention. The compound, when administering to a subject in need thereof, inhibits the IRES translation activity of an infectious virus while leaving the CAP-dependent translation activity of the subject unaffected.

Moreover, the invention features a packaged product including a container, an effective amount of a compound that inhibits the IRES translation activity of an infectious EV or EMCV without affecting the CAP-dependent translation activity of a host subject, and a legend associated with the container and indicating administration of the compound for treating EV or EMCV infection.

This invention also features a translation regulating system comprising (a) a bicistronic DNA construct containing IRES of EV or EMCV, wherein said bicistronic DNA construct containing IRES of EV or EMCV comprises in sequence, a first reporter gene, which is CAP-dependent initiated, and a second reporter gene, which is IRES-dependent initiated; and (b) an amount of amantadine; wherein said amount of amantadine inhibits the IRES-dependent translation activity in a dose-dependent manner without interfering the CAP-dependent translation.

This invention further features a method of regulating translation by use of a translation regulation system prepared according to this invention, wherein said system comprising:

(a) a bicistronic DNA construct containing IRES of EV or EMCV, wherein said bicistronic DNA construct containing IRES of EV or EMCV comprises in sequence, a first reporter gene, which is CAP-dependent initiated, and a second reporter gene, which is IRES-dependent initiated; and (b) an amount of amantadine;

Said method comprising the steps of:

1) selecting a suitable amount of amantadine; and 2) contacting the selected amount of amantadine with a host cell transfected with the bicistronic DNA construct containing IRES of EV or EMCV;

wherein said selected amount of amantadine inhibits IRES-dependent translation activity of the transfected DNA construct to a desired degree without significant impacts on the CAP-dependent translation activity of the host cell.

The details of one or more embodiments of the invention are set forth in the accompanying description and drawings below. Other features and advantages of the invention will be apparent from the detail descriptions, and from claims.

It is to be understood that both the foregoing general description and the following detailed description are by examples, and are intended to provide further explanation of the invention as claimed.

DESCRIPTION OF THE PREFERRED EMBODIMENTS

Figure 1:
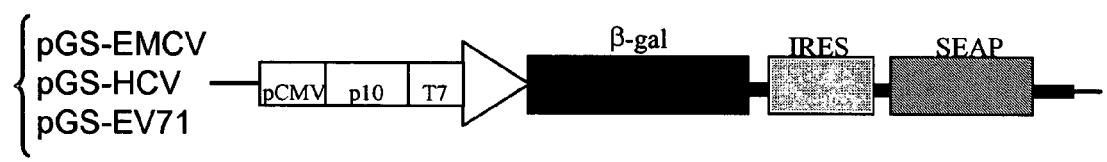
FIG. 1 illustrates the DNA organization of the bicistronic DNA constructs containing IRES of EV71, EMCV or HCV according to Example 1 of this invention.

This invention is based on the discovery that bicistronic DNA constructs containing IRES of EV or EMCV are useful in identifying compounds that inhibit the IRES-dependent translation activity of an infectious virus while leaving the CAP-dependent translation activity of a host subject unaffected.

To identify compounds that inhibit EV or EMCV gene expression or protein activity level in a subject, a system containing a bicistronic DNA construct is contacted with a candidate compound, wherein said bicistronic DNA construct comprises in sequence, a first reporter gene, which is CAP-dependent initiated, and a second reporter gene, which is IRES-dependent initiated; and a level of said first reporter gene and said second reporter gene expression or protein activity in the system is determined, if the level of the first reporter gene expression or protein activity is relatively unaffected while at the same time the level of the second reporter gene expression is significantly reduced, indicates that the candidate compound inhibits the IRES translation activity without affecting the CAP-dependent translation.

Bicistronic DNA constructs of this invention are prepared by methods well known in the art. For example, a pTriEx-4 plasmid comprising thereon three promoters (i.e., CMV, T7 and P10), is used as a template for constructing the bicistronic DNA constructs with sequences arranged in the following order: promoter sequences; a sequence encoding a first reporter protein, with a stop codon encoded at the 3'-end of such sequence; a sequence encoding an IRES element, such as IRES selected from the group consisting of enterovirus, rhinovirus, encephalomyocarditis virus, cardiovirus, aphthovirus, hepatitis A virus, hepatitis B virus, hepatitis C virus or some other picornavirus IRES sequences; and a sequence encoding a second reporter protein.

CAP-dependent and IRES-dependent translation can be studied in either intact cells system or in cell-free system. In intact cells system, cells are transfected by procedures well known in the art with bicistronic DNA constructs described above. The candidate compounds are then tested to determine their impact on levels of reporter proteins translated via CAP-dependent and IRES-dependent translation. A compound that inhibits IRES-dependent translation without interfering CAP-dependent translation is potentially a compound useful in preparing a medicament for treating viral infection. In cell-free system, bicistronic RNAs can be prepared by in vitro transcription of said bicistronic DNA constructs described above follows by in vitro translation of proteins from RNAs encoding such proteins in a system containing all necessary elements (e.g., ribosomes, tRNAs, amino acids, salts and various other factors) required to sustain protein syntheses. Such system typically contains mixtures prepared from sources such as HeLa cells or *E. Coli* cells.

Proteins suitable for use as reporter proteins in the methods of this invention include, but are not limited to, easily assayed enzymes such as β-galactosidase (β-gal), luciferase (Luc), β-glucuronidase (GUS), chloramphenicol acetyl transferase (CAT), and secreted embryonic alkaline phosphatase such as secreted human placental alkaline phosphatase (SEAP); proteins for which immunoassays are readily available such as hormones and cytokines; proteins which confer a selective growth advantage on cells such as adenosine deaminase, aminoglycoside phosphotransferase (the product of the neo gene), dihydrofolate reductase, hygromycin-B-phosphotransferase, thymidine kinase (when used with HAT medium i.e., a medium containing hypoxanthine, aminopterin and thymidine), xanthine-guanine phosphoribosyltransferase (XGPRT), proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin, botulism toxin, scorpion neurotoxin or diphtheria toxin. Methods of measuring protein levels are also well known in the art.

The candidate compounds can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one compound" libraries. See e.g., Zuckermann et al., (1994) J Med Chem 37, 2678-2685; and Lam (1997) Anticancer Drug Des 12, 145.

Examples of methods for the synthesis of molecular libraries can be found in the art, for example, in DeWitt et al., (1993) PNAS USA 90, 6909; Erb et al., (1994) PNAS USA 91, 11422; Zuckermann et al., (1994) J Med Chem 37, 2678; Cho et al., (1993) Science 261, 1303; Carrell et al., (1994) Angew Chem Int Ed Engl 33, 2059; Carrell et al., (1994) Angrew chem. Int Ed Engl 33, 2061; and Gallop et al., (1994) J Med Chem 37, 1233. Methods of making monoclonal and polyclonal antibodies and fragments thereof are also known in the art. See, for example, Harlow and Lane, (1998) Antibodies: A Laboratory Manual, Cold Spring Harbor Laboratory, New York. The term "antibody" includes intact molecules and fragments thereof, such as Fab, $F(ab')_2$, and Fv which are capable of binding to an epitopic determinant present in the reporter proteins.

Libraries of compounds may be presented in solution (e.g., Houghten (1992) Biotechniques 13, 412-421), or on beads (Lam (1991) Nature 354, 82-84), chips (Fodor (1993) Nature 364, 555-556), bacteria (U.S. Pat. No. 5,223,409), spores (U.S. Pat. No. 5,223,409), plasmids (Cull et al., (1992) PNAS USA 89, 1865-1869), or phages (Scott and Smith (1990) Science 249, 386-390; Devlin (1990) Science 249, 404-406; Cwirla et al., (1990) PNAS USA 87, 6378-6382; Felici (1991) J Med Biol 222, 301-310; and U.S. Pat. No. 5,223,409).

A compound identified by the method of this invention is amantadine. Amantadine, developed in the 1960s, has diverse uses that range from prevention of influenza A infection to the treatment of Parkinson's disease. See Aoki and Sitar, (1988) Clin Pharm 14, 35-51. While an understanding of the precise mechanism is not necessary to carry out the methods of this invention, it is believed that amantadine selectively binds to specific IRES RNA conformation or factors that mediate the IRES-dependent translation, such as La protein or PTB, and thereby blocks events in IRES-dependent translation. 1-Aminoadamantane (amantadine hydrochloride) is available commercially as an antiviral agent under the name Symmetrel (E. I. Du Pont de Nemours and Company, Wilmington, Del.). Amantadine hydrochloride may also be prepared by the methods known in the art, e.g., as described in U.S. Pat. No. 3,310,469. The present invention also contemplates the use of amantadine derivatives. For example, the (1-) position of adamantane has also been substituted with —$CH(CH_3)NH_2$ (U.S. Pat. No. 5,599,998). The resulting compound is available commercially under the name Rimantadine, which is also used in the treatment and prevention of influenza A infection.

Once a compound being identified by the method of this invention, it can be formulated in pharmaceutically acceptable composition to be administered alone or in combination with other therapeutic agents. Other therapeutic agents include, but are not limited to, antiviral agents such as interferon or ribavirin.

This invention thus further provides a method for treating EV or EMCV infection by administering a pharmaceutical composition comprising a pharmaceutically acceptable carrier and a therapeutically effective amount of a compound identified above, e.g., amantadine, to a subject. The term "treating" is defined as administering of a pharmaceutical composition described above to a subject, who has an EV or EMCV infection, with the purpose to cure, alleviate, relieve, remedy, prevent or ameliorate the infection, the symptom of the infection, or the disease state secondary to the infection. "A therapeutically effective amount" is an amount of the pharmaceutical composition that is capable of producing a medically desirable result, e.g., as described above, in a treated subject. The composition can be used alone or in combination with other therapeutically agents. These compositions can be utilized in vivo, ordinarily in a mammal, preferably in a human, or in vitro. In employing them in vivo, the compositions can be administered to the mammal in a variety of ways, including parenterally, intravenously, subcutaneously, intramuscularly, colonically, rectally, vaginally, nasally, orally, transdermally, topically, ocularly, intraperitoneally, or as suitably formulated surgical implants employing a variety of dosage forms. Preferably, amantadine is administered by the oral route, thus potentially improves patient safety and compliance.

As will be readily apparent to one skilled in the art, the useful in vivo dosage to be administered and the particular mode of administration will vary depending upon the mammalian species treated, and the particular composition employed. The determination of effective dosage levels, that is the dosage levels necessary to achieve the desired result, will be within the ambit of one skilled in the art. Typically, applications of compositions are commenced at lower dosage levels, with dosage level being increased until the desired effect is achieved. The dosage for the compositions of the present invention can range broadly depending upon the route of administration; the nature of the formulation; type of the infection; the subject's size, weight, surface area, age and sex; other drugs being administered; and the judgment of the attending physician. Typically, suitable dosages are in the range of about 0.01 mg/Kg to about 10 mg/kg, preferably between about 0.1 and 1 mg/kg, body weight.

Orally-administered formulations can be prepared in conventional forms, including capsules, chewable tablets, enteric-coated tablets, syrups, emulsions, suspensions, or as solid forms suitable for solution or suspension in liquid prior to administration. Suitable pharmaceutically acceptable carriers include, but are not limited to, water, saline, dextrose, alcohols, gum Arabic, vegetable oils, benzyl alcohols, polyethylene glycols, gelatine, carbohydrates such as lactose, amylose, or starch, magnesium stearate, talc, silicic acid, fatty acid monoglycerides and diglycerides, hydroxymethyl cellulose, polyvinyl pyrrolidone or the like. In addition, if desired, the pharmaceutical compositions may contain minor amounts of nontoxic auxiliary substances, such as wetting agents, lubricants, preservatives, pH buffering agents, stabilizers, emulsifier, salts for adjusting osmotic pressure, coloring, flavoring, and/or aromatic substances and the like which do not deleteriously react with the active compounds. If desired, absorption enhancing preparations (e.g., liposomes) may be utilized.

For parenteral application, particularly suitable are injectable, sterile solutions, preferably oily or aqueous solutions, as well as suspensions, emulsions, or implants including suppositories. Nebulizers and inhalation aerosols may also be used. Ampules are in convenient uint dosages. It is also possible to freeze-dry the compounds and use the lypophilizates obtained, for examples, for the preparation of products for injection.

For other parenteral applications, such as topical applications and non-sprayable forms, viscous to semi-solid or solid forms comprising a carrier compatible with topical application and having a dynamic viscosity preferably greater than water. Suitable formulations include but are not limited to transdermal patches, solutions, suspensions, emulsions, creams, ointments, powders, liniments, salves, aerosols, etc., which are, if desired, sterilized or mixed with auxiliary agents, e.g., preservations, stabilizers, wetting agents, buffers, or salts for influencing osmotic pressure, etc.

Also suitable for topical application are sprayable aerosol preparations wherein the identified compound, e.g., amantadine, preferably in combination with a solid or liquid inert carrier material, is packaged in a squeeze bottle or in admixture with pressurized volatile, normally gaseous propellant. The application of these embodiments can be to the skin or mucous membrane or in the interior of the body and can be oral, peroral, enteral, pulmonary, rectal, nasal, vaginal, lingual, intervenous, intraarterial, intracardial, intramuscular, intraperitoneal, intracutaneous, subcutaneous. The parenteral preparations are preferably sterile or sterilized products.

In this manner, U.S. Pat. No. 4,895,727 to Allen, herein incorporated by reference, describes a method of inducing a reservoir effect in skin and mucous membranes so as to enhance penetration and retention and reduce transdermal flux of topically applied therapeutic and cosmetic pharmacologically active agents. U.S. Pat. No. 4,557,934 to Cooper, herein incorporated by reference, describes topical pharmaceutical compositions containing a pharmaceutically-active agent and the penetration enhancing agent, 1-dodecylazacycloheptan-2-one. This composition provides marked transepidermal and percutaneous delivery of the selected pharmaceutically-active agent.

Suppositories containing amantadine can be created using a suitable oleaginous or water-soluble base. The oleaginous class includes cocoa butter and fats with similar properties the water-soluble class includes polyethylene glycols.

Other medicaments containing the identified compound, e.g., amantadine, can be produced in a known manner, whereby the known and customary pharmaceutical adjuvants as well as other customary carrier and diluting agents can be used. Examples include, but are not limited to, gelatins, natural sugars such as sucrose or lactose, lecithin, pectin, starch (for example cornstarch), alginic acid, talc, lycopodium, silica (for example colloidal silica), glucose, cellulose, cellulose derivatives for example, cellulose ethers in which the cellulose hydroxyl group are partially etherified with lower aliphatic alcohols and/or lower saturated oxyalchohols, for example, methyl hydroxypropyl cellulose, methyl cellulose, cellulose phthalate, stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium palmitate, and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g. glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydricaliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g. glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane).

Other adjuvants can also be substances that bring about decomposition (so-called explosives) such as: cross-linked polyvinyl pyrrolidone, sodium carboxy methyl starch, sodium carboxy methyl cellulose or microcrystalline cellulose. Likewise, known coating agents such as e.g. polyacrylates, cellulose ethers and the like can be used.

For the production of solutions, there can be used water of physiologically compatible organic solvents, as for example, ethanol, 1,2-propylene glycol, polyglycols, e.g., diethylene glycol, triethylene glycol and dipropylene glycol and their derivatives dimethyl sulfoxide, fatty alcohols, e.g., stearyl alcohol, cetyl alcohol, lauryl alcohol and oleyl alcohol, triglycerides, e.g. glyceryl olelate glyceryl stearate, glyceryl palmitate, and glyceryl acetate, partial esters of glycerine, e.g., glyceryl monostearate, glyceryl distearate, glyceryl monopalmitate, paraffins, and the like.

For injectable solutions or suspensions, non-toxic parenterally compatible diluting agents or solvents can be used, for example: Water, 1,3 butane diol, ethanol, 1,2-propylene glycol, polyglycols in a mixture with water, Ringer's solution, isotonic solution of sodium chloride or also hardened oils including synthetic mono or diglycerides or fatty acids like oleic acid.

Known and customary solution assistants or emulsifiers can be used in the production of the preparations. The following are examples of solution assistants and emulsifiers which can be used: Polyvinylpyrrolidone, sorbitan fatty acid esters such as sorbian trioleate, phosphatides such as lecithin, acacia, tragacath, polyoxethylated sorbitan monooleate and other ethoxyated fatty acid esters of sorbitan, polyoxyethylated fats, polyoxyethylated oleotriglycerides, linolized oleotriglycerides, or polyethylene oxide condensation products of fatty alcohols. The term polyoxyethylated means in this context that the substances in question contain polyoxyethylene chains whose polymerization is generally between 2 to 40 and especially between 10 to 20.

Such polyoxyethylated substances can be obtained, for example, by reacting compounds containing hydroxyl groups (e.g. mono or diglycerides or unsaturated compounds such as, e.g., those containing the oleic acid residues) with ethylene oxide (e.g. 40 moles ethylene oxide per mole glyceride). Examples of oleotriglycerides are olive oil, peanut oil, castor oil, sesame oil, cotton seed oil and corn oil. See also Fiedler, Lexicon der Hilfastoffe fur Pharmazie, Kosmetik and Angrezende Gebiete, Lexicon of Adjuvants for Pharmacy, Cosmetics an Related Areas pp. 191-195 (1971).

Furthermore, there can be added preservatives stabilizers, buffers, for example, calcium hydrogen phosphate, colloidal aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium-meta bisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

The materials and methods of the present invention will now be illustrated by examples only with reference to the following non-limiting examples. Further embodiments will be apparent to those skilled in the art in the light of these.

EXAMPLE 1

Construction of Bicistronic DNA Constructs

Plasmid pGS-EMCV is constructed by inserting into the plasmid pTriEx-4 (obtained from Novagene) template sequences of two reporter genes (cistrons), i.e., β-galactosidase (β-gal), and secreted human placental alkaline phosphatase (SEAP), with a promoter upstream of the first cistron (i.e., β-gal) and an EMCV-IRES sequence downstream of it, between the first cistron and the second cistron (i.e., SEAP). Plasmid pGS-EV71 and pGS-HCV are prepared in similar manner except an EV71-IRES sequence or a HCV-IRES sequence was used to replace the EMCV-IRES sequence. FIG. 1 shows the DNA organization of the bicistronic DNA constructs containing IRES of EV71, EMCV and HCV, respectively.

EXAMPLE 2

Identifying Compounds That Inhibit IRES-Dependent Translation

Transfection

The kidney cells from African green monky, i.e., Cos-1 cells, were transfected with the bicistronic DNA constructs prepared according to Example 1. The method of transfection is well known in the art. Briefly, a transfecting stock solution was prepared as follows: 1) solution A: 1 µg of the bicistronic DNA constructs of Example 1 was dissolved in serum free culturing medium, with its final volume adjusted to be 50 µl; 2) solution B: 2 µl of lipofectAMINE 2000 (obtained from Invitrogen) was mixed with 50 µl of serum free culturing medium; 3) mixed solution A with solution B. Cos-1 cells (0.5-2×10$^5$/well, 24 wells) were first incubated with 500 µl of the serum free culturing medium for a period of 20 min, and then 102 µl of the transfecting stock solution prepared above was added. The transfected cells were then return to culture environment (37° C., 5% CO$_2$). After 12 hrs, the culturing medium were replaced by a medium containing fetal bovine serum and antibiotics, the transfected cells were continued to culture for another 12 hrs before used in the following compound screening procedure.

Compound Screening

The candidate compounds prepared according to the methods described above were dissolved in PBS, with stock concentration to be 10 mg/ml. These stock solutions were then diluted to proper ranges according to various screening conditions required. Briefly, the various diluted tested compound solutions were added to the transfected cells respectively, and incubated for a period of 12 hrs, then the cells were lysed and the reporter proteins activities (i.e., β-gal and SEAP) were measured to determine whether the tested compound inhibit IRES-dependent translation (i.e., the level of SEAP) or CAP-dependent translation (i.e., the level of β-gal). If the level of SEAP is significantly reduced while the level of β-gal is relatively unchanged, it indicates that the tested compound is a useful agent in suppressing infectious EV or EMCV activity without interfering the CAP-dependent translation activity of the host cells. Then, the identified tested compound can be used in preparation of a medicament for treating EV or EMCV infection.

Assay of Protein Activity

Reporter proteins activities, i.e., secreted Human Alkaline Phosphatase (SEAP) and β-galactosidase (β-gal), were measured with BD Great EscApe SEAP Detection kit (Cat. No. K2041-1, available from Clontech) and Luminescent β-gal Detection kit (Cat. No. K2048-1, available from Clontech), respectively, according to the manufacturer's instruction.

Amantadine Inhibits IRES-dependent Translation

Figure 2:
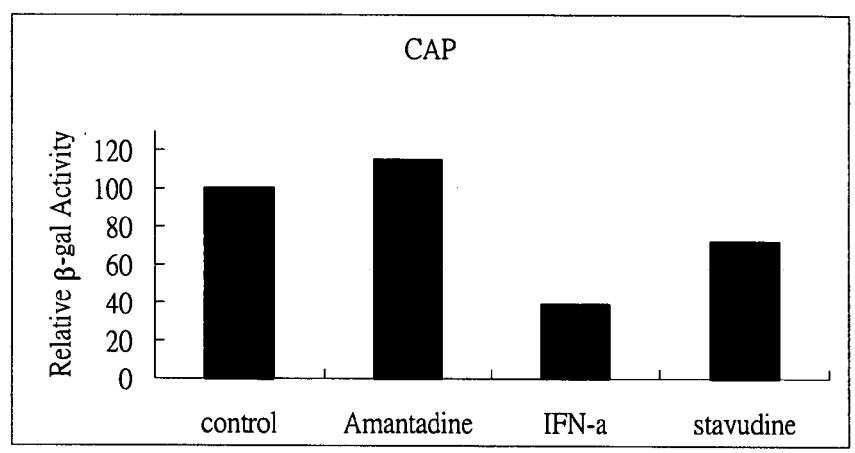
FIG. 2 illustrates the effects of three candidate compounds on β-galactosidase (FIG. 2A) or SEAP (FIG. 2B) activities of cells transfected with bicistronic DNA constructs containing IRES of EV-71, the normalized SEAP activity is provided in FIG. 2C; the concentration of each candidate compound is as follows: amantadine, 0.1 mg/ml; IFN-α, 10 units; and stavudine, 0.05 mg/ml.
Figure 2:
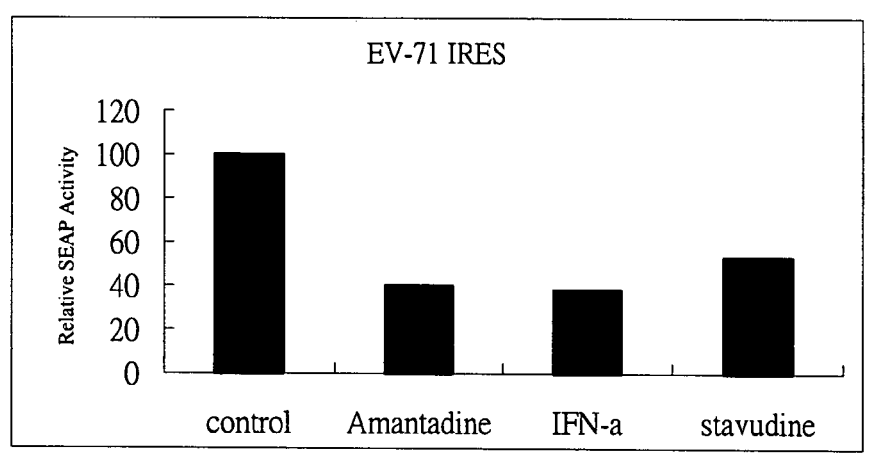
Figure 2:
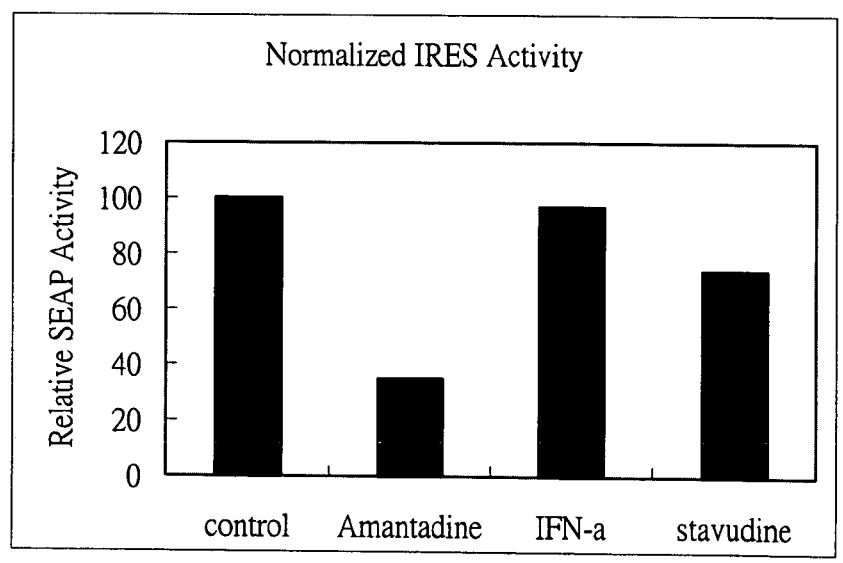

Several candidate compounds are selected, including amantadine, INF-α and stavudine, and were tested on cells transfected with bicistronic DNA constructs of Example 1 according to procedures described above. SEAP and β-gal activities were assayed to determine if any of these candidate compounds is a potential compound for treating EV or EMCV infection. Results are provided in FIG. 2. It is clear from the screening process that among the 3 selected and tested candidate compounds, only amantadine demonstrates selective inhibition on IRES-dependent translation without affecting CAP-dependent translation. This preliminary screening result indicates that amantadine is a potential compound for treating an EV or EMCV infection. Detail analysis of amantadine is provided below.

Figure 3:
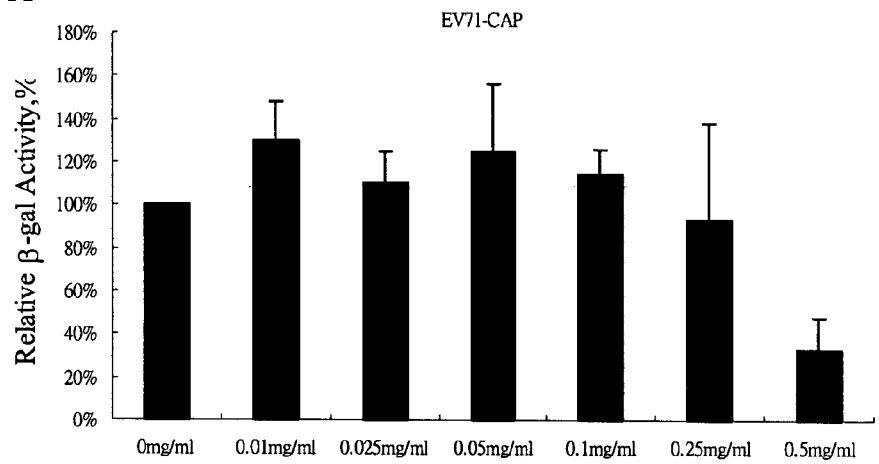
FIG. 3 illustrates the effects of amantadine on β-galactosidase (FIG. 3A) or SEAP (FIG. 3B) activities of cells transfected with bicistronic DNA constructs containing IRES of EV71, the normalized SEAP activity is provided in FIG. 3C.
Figure 3:
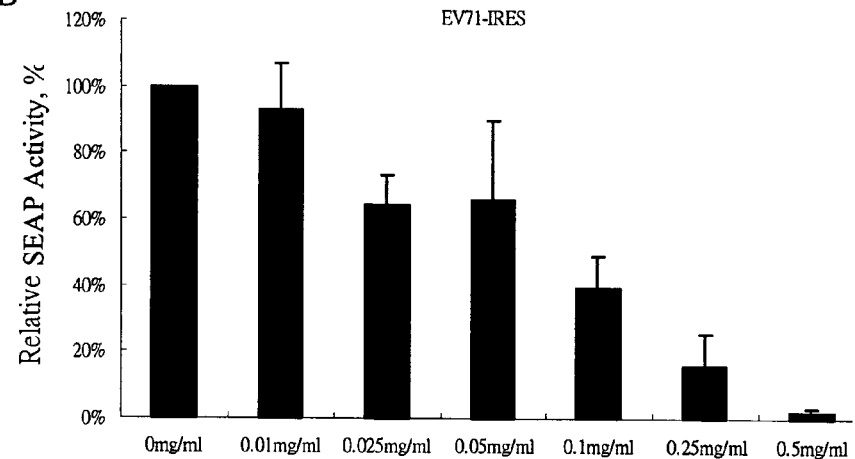
Figure 3:
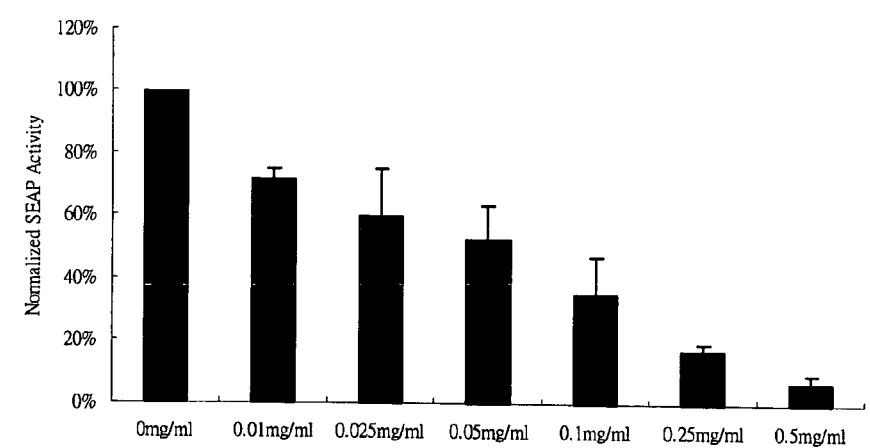
Figure 4:
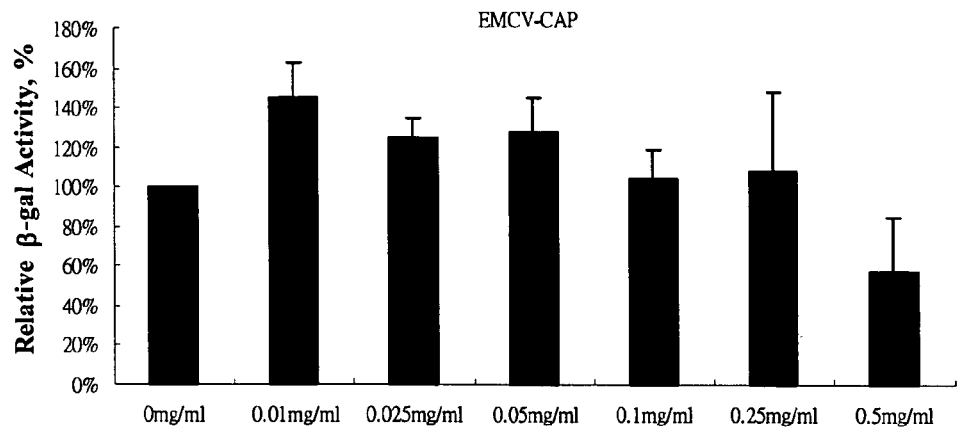
FIG. 4 illustrates the effects of amantadine on β-galactosidase (FIG. 4A) or SEAP (FIG. 4B) activities of cells transfected with bicistronic DNA constructs containing IRES of EMCV, the normalized SEAP activity is provided in FIG. 4C.
Figure 4:
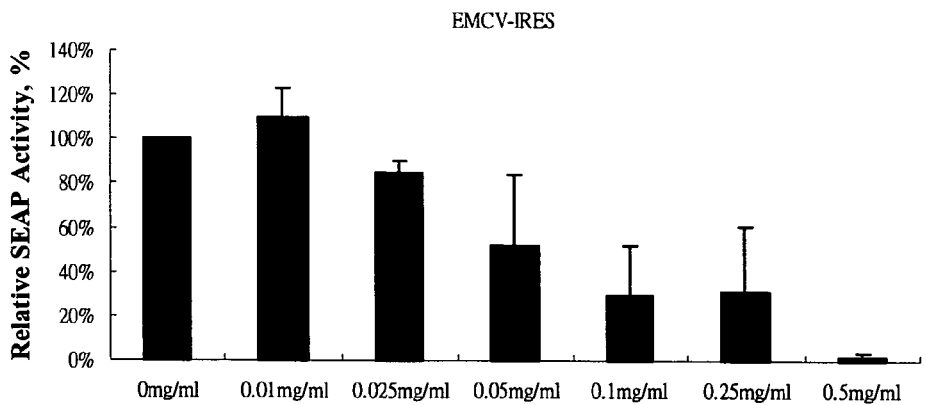
Figure 4:
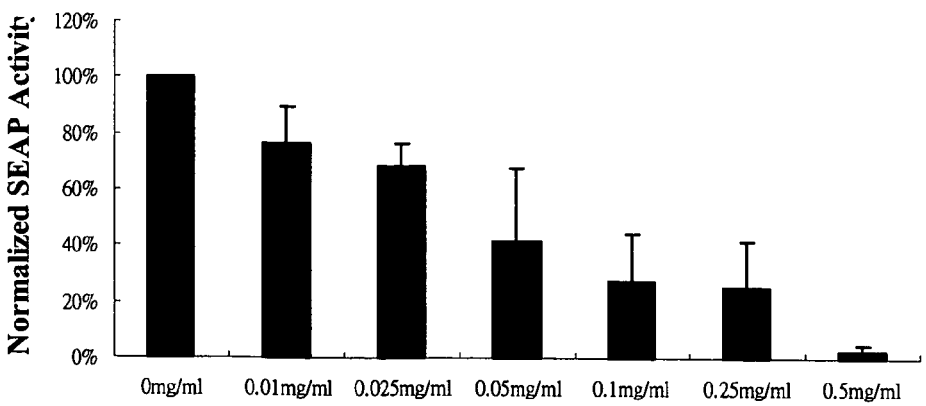

Amantadine, was tested on cells transfected with bicistronic DNA constructs of Example 1 according to procedures described above. SEAP and β-gal activities were assayed to determine the dose relationship of amantadine on gene expression. Screening results using bicistronic DNA constructs containing IRES of EV71 and EMCV were provided in FIGS. 3 and 4, respectively. Amantadine, ranges from 0.01 mg/ml to 0.25 mg/ml, possesses little or no effect on the β-gal activities in cells transfected with either pGS-EV71 or pGS-EMCV DNA (FIG. 3A and FIG. 4A). On the contrary, amantadine at the same ranges inhibits SEAP activities in the cells transfected with either pGS-EV71 or pGS-EMCV DNA (FIG. 3B and FIG. 4B). Particularly, amantadine at dose of 0.25 mg/ml, inhibits about 80% of IRES-dependent translation activity while possesses relatively no effect on CAP-dependent translation activity (FIGS. 3 and 4). The normalized SEAP activity showed the inhibition of amantadine is in a dose dependent relationship (FIGS. 3C and 4C) and the calculated IC$_{50}$ for inhibition of IRES-dependent translation of EV71 or EMCV is about 0.055 mg/ml or 0.045 mg/ml, respectively. Furthermore, the IC$_{50}$ for EV-71 whole cell antiviral activity of amantadine is about 8.82 mg/ml. It is also found that amantadine possesses no effects on IRES of HCV (hepatitis C virus) (data not shown). Taking together, the results demonstrate that amantadine is a potential drug for treating EV and EMCV infection, but not HCV infection.

Figure 5:
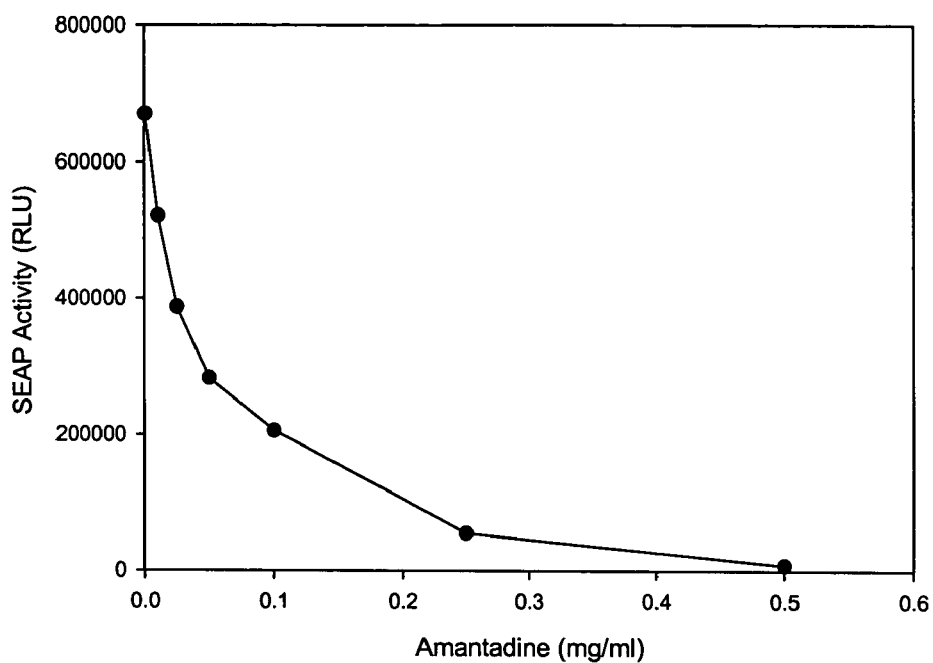
FIG. 5 illustrates the dose-dependent relationship between amantadine and EV71-IRES mediated (FIG. 5A) or EMCV-IRES mediated (FIG. 5B) gene expression in a translation regulation system comprises amantadine and bicistronic DNA constructs containing IRES of EV71 or EMCV.
Figure 5:
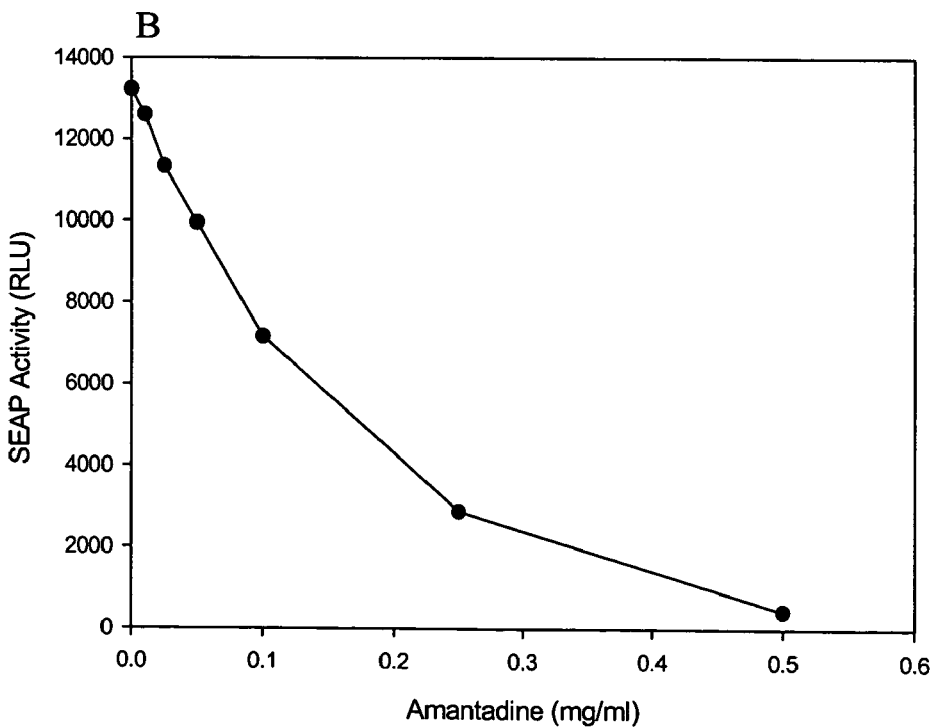

Use of Amantadine and Bicistronic DNA Constructs Containing IRES of EV71 or EMCV as a Translation Regulation System The conventional translation regulation system is usually comprised of three parts: (1) a promoter such as lac promoter or TRE-CMVmin promoter; (2) protein transcription activators or repressors such as tTA transactivator or lacI repressor; and (3) a regulator usually of small molecule that are capable of controlling the binding activities between said protein transcription activators or repressors and said DNA promoter, such as IPTG or tetracycline. Based on the findings of this invention, a more simplified translation regulation system is obtained by taking advantages of the unique property of amantadine and the bicistronic DNA constructs containing IRES of EV71 or EMCV. The regulatory function of amantadine on EV71-IRES mediated or EMCV-IRES mediated gene expression in a translation regulation system comprises of amantadine and bicistronic DNA constructs containing IRES of EV71 or EMCV is illustrated in FIG. 5, where amantadine exhibited dose dependent inhibition on either EV71-IRES mediated or EMCV-IRES mediated gene expression. Based on this finding, any skilled person in the relevant art may select a particular does of amantadine, applies it to cells transfected with bicistronic DNA constructs containing IRES of EV71 or EMCV, and obtains a desirable degree of inhibition to a gene that are linked to IRES sequence. As exemplified by the results of FIG. 5, in the system containing an EV71-IRES, a 20% gene inhibition was achieved by use of amantadine at a dose of about 0.01 mg/ml, whereas a 80% gene inhibition was achieved at a dose of about 0.25 mg/ml. Similarly, in the system containing an EMCV-IRES, a 20% or 80% gene inhibition was obtained at a dose of amantadine of about 0.05 mg/ml or 0.25 mg/ml, respectively.

Although the present invention has been described in considerable detail with reference to preferred embodiments thereof, however, other embodiments are possible for those skilled in the art and various modifications and variations can be made to the niosome of the present invention without departing from the scope or spirit of the invention. In view of the foregoing, it is intended that the present invention cover modifications and variations of this invention provided they fall within the scope of the following claims and their equivalents.

What is claimed is:

1. A translation regulating system comprising:
   (1) a bicistronic DNA construct containing IRES of enterovirus (EV), wherein said bicistronic DNA construct comprises in sequence, a first reporter gene, which is CAP-dependent initiated, and a second reporter gene, which is IRES-dependent initiated; and
   (2) an amount of amantadine;
   wherein said amount of amantadine inhibits the IRES-dependent translation activity in a dose-dependent manner without interfering the CAP-dependent translation.

2. A method of regulating translation by use of the translation regulating system of claim 1, wherein said method comprising the steps of:
   (1) selecting a suitable amount of amantadine; and
   (2) contacting the selected amount of amantadine with a host cell transfected with the bicistronic DNA construct containing IRES of enterovirus (EV);
   wherein said selected amount of amantadine inhibits IRES-dependent translation activity of the transfected DNA constructs to a desired degree without significant impacts on the CAP-dependent translation activity of the host cell.

3. The system of claim 1, wherein the amount of amantadine is between 10 µg/ml to 100 µg/ml.

4. The system of claim 1, wherein the amount of amantadine is between 10 µg/ml to 100 µg/ml.

* * * * *